United States Patent [19]

Arena

[11] 4,413,152

[45] Nov. 1, 1983

[54] HYDROGENATION IN AQUEOUS SOLUTIONS

[75] Inventor: Blaise J. Arena, Des Plaines, Ill.

[73] Assignee: UOP Inc., Des Plaines, Ill.

[21] Appl. No.: 411,156

[22] Filed: Aug. 25, 1982

[51] Int. Cl.$^3$ .................... C07C 31/26; C07C 31/24; C07C 31/18

[52] U.S. Cl. .................................. 568/863; 502/332; 502/334

[58] Field of Search ........................................ 568/863

[56] References Cited

U.S. PATENT DOCUMENTS

| | | | |
|---|---|---|---|
| 1,963,999 | 6/1934 | Larchar | 568/863 |
| 2,868,847 | 1/1959 | Boyers | 568/863 |
| 3,963,788 | 6/1976 | Kruse et al. | 568/863 |
| 3,963,789 | 6/1976 | Kruse et al. | 568/863 |
| 4,072,628 | 2/1978 | Kruse et al. | 568/863 |

*Primary Examiner*—J. E. Evans
*Attorney, Agent, or Firm*—James R. Hoatson, Jr.; Eugene I. Snyder; William H. Page, II

[57] ABSTRACT

Zerovalent Group VIII metals dispersed on titanated alumina are hydrothermally stable hydrogenation catalysts which may be used advantageously in the reduction of aqueous solutions of carbohydrates. The use of ruthenium on titanated alumina in the hydrogenation of glucose affords sorbitol in excellent yields with quite high selectivity, and with minimal leaching of either ruthenium, titanium, or alumina.

11 Claims, No Drawings

HYDROGENATION IN AQUEOUS SOLUTIONS

BACKGROUND OF THE INVENTION

In hydrogenating organic materials using zerovalent metal catalysts, it is more common to use the metal dispersed on an inert support than to use, for example, colloidal dispersions of the metal itself. Included among advantages accuring to supported metals are their greater surface activity, leading to increased reactivity, and their greater ease of separation, as by filtration. Colloidal metals are notoriously difficult to separate by filtration, and incomplete removal and recovery is costly and often deleterious to the product of hydrogenation.

When hydrogenations are conducted in aqueous media, the low hydrothermal stability of the commonly used supports places severe limitations on catalyst lifetime and recovery and also on the quality of the product due to dissolved support material. Where such hydrogenations are of hydroxylic organic compounds, the problem of hydrothermal instability of support materials is intensified. Where the organic compounds are polyhydroxylic, such as carbohydrates, the problem of hydrothermal instability is particularly exacerbated because of the relatively high concentration of hydroxyl groups from both water as solvent and the material to be hydrogenated.

The challenge in hydrogenating carbohydrates arises because many reduction products are important materials of commerce—sorbitol and mannitol are but two common reduction products—which must be prepared via hydrogenation in aqueous media because carbohydrates generally are insoluble or, at best, sparingly soluble in most organic solvents. Because carbohydrates are solids, it is operationally mandatory to use a solvent in their hydrogenation.

It is an object of this invention to set forth a general method of hydrogenation in aqueous solution. A particular embodiment is the hydrogenation of carbohydrates in aqueous media using as a catalyst a zerovalent metal on a hydrothermally stable support. A more particular embodiment comprises a method of hydrogenating an aqueous solution of a carbohydrate where the catalyst is a Group VIII zerovalent metal dispersed on a support of titanated alumina. In a still more specific embodiment the metal is ruthenium. In a yet more specific embodiment the carbohydrate is a hexose.

DESCRIPTION OF THE INVENTION

The invention which is the subject matter herein is a method for the hydrogenation of a water soluble hydrogenatable organic compound comprising contacting at hydrogenation conditions an aqueous solution of the organic compound with hydrogen and a catalyst consisting essentially of a zerovalent Group VIII metal selected from the group consisting of osmium, ruthenium, rhodium, nickel, palladium, and platinum dispersed on titanated alumina, and recovering the formed hydrogenation product. In a particularly important embodiment the organic compound is a carbohydrate and the hydrogenation product is the polyol(s) formed therefrom.

This invention results from the discovery that titanated alumina possesses remarkable hydrothermal stability under conditions necessary for the hydrogenation of aqueous solutions of carbohydrates, especially in comparison with the more commonly used gamma-alumina. Thus, whereas substantial amounts of silica and gamma-alumina, which are two commonly employed support materials, dissolve in the aqueous medium during hydrogenation of carbohydrates, virtually no leaching of titanated alumina occurs under comparable hydrogenation conditions.

Therefore, one advantage of this invention is that the product contains a substantially lower level of dissolved metal from the inert support described herein than that resulting from inert supports commonly employed previously in the hydrogenation of carbohydrates.

Another advantage of this invention is that the zerovalent metals commonly employed as a hydrogenation catalyst retain their activity on the titanated alumina support of this invention.

Yet another advantage offered by the Group VIII metals platinum, palladium, rhodium, osmium, and ruthenium is their increased resistance to leaching under hydrogenation conditions relative to other metals of this class, such as nickel. Because ruthenium is both resistant to leaching and particularly active catalytically it is especially advantageous in the practice of this invention.

As mentioned previously, one embodiment of the invention herein is concerned with a method of hydrogenating a carbohydrate to its polyol(s). Carbohydrates are polyhydroxaldehydes, polyhydroxyketones, or compounds that can be hydrolyzed to them. A carbohydrate that cannot be hydrolyzed to simpler compounds is called a monosaccharide. One that can be hydrolyzed to two monosaccharide molecules is called a disaccharide, and one that can be hydrolyzed to many monosaccharide molecules is called a polysaccharide. A monosaccharide may be classified according to the number of carbon atoms it contains; a hexose is a 6-carbon monosaccharide, a pentose is a 5-carbon monosaccharide, and a tetrose is a 4-carbon monosaccharide. Monosaccharides are preferred among the carbohydrates which may be used in this invention, and among these the hexoses, pentoses and tetroses are the most important members, with the hexoses particularly preferred.

The polyol reduction products of this invention have the formula $HOCH_2(CHOH)_nCH_2OH$, where n is 2, 3, or 4 depending upon the kind of monosaccharide used or the kind of units in the di- or polysaccharide. Where n is 4, the polyol is a hexitol; where n is 3, the polyol is a pentitol; and where n is 2, the polyol is a tetritol. It is to be understood that where the carbohydrate is a disaccharide or polysaccharide, substantial hydrolysis accompanies hydrogenation to ultimately afford the polyols of this invention.

The examples of carbohydrates below are cited merely for illustration, and are not intended as exhaustive of the suitable reactants which may be used in this invention. Accordingly, monosaccharides that can be employed include glucose, mannose, galactose, talose, fructose, allose, altrose, idose, gulose, xylose, lyxose, ribose, arabinose, threose and erythrose. Glucose and mannose are particularly preferred monosaccharides which afford sorbitol and mannitol, respectively, as their polyol reduction product. Fructose is another preferred monosaccharide which affords a mixture of sorbitol and mannitol as the product. Examples of disaccharides include maltose, cellobiose, sucrose and lactose. Among the more abudant polysaccharides which may be employed in this invention are starch, cellulose and their degradation products.

The catalysts of this invention consist essentially of a zerovalent Group VIII metal dispersed on titanated alumina. Among the metals which may be used are included ruthenium, osmium, rhodium, nickel, palladium and platinum, with ruthenium being preferred because of its high resistance to leaching and particularly high catalytic activity under process conditions.

The Group VIII metal is generally dispersed on titanated alumina as the inert support by impregnating the latter with a suitable salt of the metal, calcining the salt where necessary, and by reducing it to the zerovalent metal in a hydrogen atmosphere. Calcining is performed where volatiles are to be removed from the support, or where the metal salt needs to be converted, e.g., to its oxide, to be readily reducible. In suitable cases calcination and reduction may be combined in the same step. The activity of the catalyst depends somewhat upon the reduction temperature. Thus, although suitable catalysts may be prepared by reducing the metal in hydrogen at a temperature between about 100° C. and 600° C., a somewhat more active catalyst is obtained at a temperature from about 150° C. to about 300° C. Metal loadings between about 1 and 10% are most commonly employed.

By "titanated alumina" is meant an alumina prepared by treating alumina with a titanium tetrahalide under conditions where the titanium-halogen bond is not hydrolyzed, removing adhering but unreacted excess $TiX_4$, then oxidizing the material obtained thereby at a temperature from about 100° C. to about 500° C. The resulting material can thereafter be steam treated to remove halide ions. Titanium tetrachloride is the tetrahalide of choice, although the bromide or fluoride may be used, but not necessarily with equivalent results.

The titanated alumina of this invention may be thought of as alumina whose surface hydroxyl groups have been converted to O-Ti moieties. Whatever may be the case, titanated alumina has many physical properties, e.g., surface area, apparent bulk density, etc., virtually identical to its alumina precursor even though 2-10% titanium is present. In contrast to its unaltered physical properties are some important changes in chemical properties of titanated alumina. Thus, where extensive leaching in aqueous solution of the support occurs with gamma-aluminas, titanated gamma-aluminas show excellent hydrothermal stability thereby affording the advantages accruing to this invention.

The aqueous solution of the carbohydrate is contacted with hydrogen and the catalyst of this invention at hydrogenation conditions. Hydrogenation conditions include a pressure of at least about 200 psig, with pressures in excess of about 5000 psig generally not advantageous. In the usual case, a hydrogen pressure from about 700 to about 5000 psig is used, with a pressure from about 1000 to about 3000 psig preferred. The hydrogenation temperature will be greater than about 80° C., with the upper temperature limit dictated by the onset of the decomposition of either the product or reactant. For example, in the case of glucose as the reactant and sorbitol as the product, the upper temperature limit is about 160° C. In practical terms, a hydrogenation temperature from about 100° to about 150° C. is preferred with one from about 110° to about 130° C. being especially advantageous.

The amount of catalyst used will depend, inter alia, on the amount of metal on the support, hydrogenation pressure, and temperature. In the case of ruthenium, for example, sufficient catalyst is employed to given from about 0.1 to about 1 wt. % ruthenium based on the carbohydrate as monosaccharide. The other specified metals may be used in this same weight range except for nickel, which generally is used in the range from about 0.2 to about 3 wt. percent.

The method of this invention may be practiced in either a batch or a fixed mode. In the batch mode, an aqueous solution of the carbohydrate containing from about 25 to about 60 percent carbohydrates is loaded into a reactor containing, for example, the ruthenium on titanated alumina catalyst of this invention in an amount sufficient to given from about 0.1 to about 1 wt. % ruthenium based on the carbohydrate. The mixture is then heated to the desired temperature, which is from about 80° to about 160° C., and usually from about 100° to about 150° C. After the desired reaction temperature is attained, hydrogen is admitted to a pressure from about 700 to about 5000 psig. The entire reaction mixture is then agitated to provide adequate contact among the hydrogen, catalyst, and carbohydrate. The hydrogenation is continued until there is no further hydrogen uptake, which generally is a time from about 0.5 to about 5 hours.

The invention described is advantageously practiced in a continuous fashion using the catalyst in a fixed bed, fluidized bed, expanded bed, and so forth. In a typical operation, feedstock containing from about 25 to about 60% of the carbohydrate(s) to be reduced is passed, through the bed of catalyst, which is platinum, palladium, osmium, or ruthenium on titanated alumina, in a hydrogen atmosphere. Hydrogen pressure is from about 700 to about 5000 psig, and bed temperature is generally from about 100° to about 150° C. The effluent is an aqueous solution of the formed polyol(s), which may be recovered by, for example, removal of water by evaporation.

The examples which follow merely illustrate this invention and are not intended to limit it in any way.

EXAMPLE 1

The following experiment was done to demonstrate the hydrothermal stability of various materials often used as an inert support for catalytically active zerovalent metals. A mixture of 50 ml of a 50 percent aqueous solution of sorbitol and 2.5 g of support material was held in a rotating glass-lined autoclave for 24 hours in the presence of hydrogen at 135 atmospheres (ca. 1900 psig) and at 130° C. At the end of this period, solid was removed by filtration and the filtrate was analyzed for metals. The following table summarizes the results.

| LEACHING OF INERT SUPPORTS | |
|---|---|
| Support Material | Dissolved Support Material |
| gamma-alumina[a] | 60 ppm Al |
| titanated alumina from above[b] | less than 1 ppm Ti, 3.5 ppm Al |
| kieselguhr[c] | 83 ppm Si |

[a] 0.5 ABD, surface area 200 m$^2$/g
[b] 9% Titanium
[c] Solution of glucose was used instead of sorbitol.

The results clearly show the superior hydrothermal stability of a titanated alumina relative to other commonly employed supports, especially its gamma-alumina precursor.

EXAMPLE 2

250 cc of gamma-$Al_2O_3$ spheres were placed in an $N_2$ purged vertical glass tube and covered with neat $TiCl_4$ and allowed to stand for 30 minutes and then the excess $TiCl_4$ was drained away, again under $N_2$ purge. The $TiCl_4$ saturated $Al_2O_3$ was placed in a vertical furnace tube and heated at 150° C. for approximately 1 hour under $N_2$ purge to further remove excess $TiCl_4$. This was followed by heat treatment in dry air at 500° C. for 3 hours. After cooling, the sample was steam treated to remove residual Cl by heating in moist air at 525° C. for 6 hours. Analysis showed 1.97% Ti, 0.01% Cl, and a surface area of 146 $m^2$/g.

3.2 g of $RuCl_3.3H_2O$ was dissolved in 200 ml of deionized $H_2O$. This solution was thoroughly mixed with 39.7 g of the above titanated $Al_2O_3$ followed by evaporation of the solution at approximately 120° C. The $RuCl_3$ impregnated spheres were then calcined in $N_2$ flow at 400° C. for 3 hours followed by reduction in $H_2$ flow at 400° C. for 3.5 hours to afford Catalyst A.

250 cc of gamma-$Al_2O_3$ spheres were placed in a $N_2$ purged vertical glass tube and covered with neat $TiCl_4$ and allowed to stand for 30 minutes and then the excess $TiCl_4$ was drained away, again under $N_2$ purge. The $TiCl_4$ saturated $Al_2O_3$ was placed in a vertical tube furnace and heated at 150° C. for approximately 1 hour under $N_2$ purge to further remove excess $TiCl_4$. This was followed by heat treatment in dry air to 500° C. for 3 hours. After cooling, the sample was steam treated to remove residual Cl by heating in moist air at 525° C. for 6 hours. Analysis showed 8.99% Ti, 0.09% Cl, with a surface area of 189 $m^2$/g.

7.7 g of $RuCl_3.3H_2O$ was dissolved in 200 ml of deionized $H_2O$. This solution was thoroughly mixed with 96.7 g of the above titanated support material, followed by evaporation of the solution at approximately 120° C. The $RuCl_3$ impregnated spheres were then calcined in $N_2$ flow at 400° C. for 3 hours, followed by reduction in $H_2$ flow at 250° C. for 3 hours to afford Catalyst B.

EXAMPLE 3

Continuous reductions were performed in a 7/8" I.D. vertical tube reactor with a spiral preheater and with a bed of 100 cc catalyst as prepared in Example 2. The feedstock was a 50% aqueous solution of glucose at pH about 5.5 passed downflow. Hydrogen was introduced at a 10:1 molar ratio relative to glucose. Effluent was analyzed by high pressure liquid chromatography for sorbitol, mannitol, fructose, and glucose. The following table, a composite of several runs, shows the effect of process variables on conversion and product distribution.

| | | | Continuous Reduction of Glucose | | | |
|---|---|---|---|---|---|---|
| Cata- | | | | Con- ver- | sor- | Selectivity[f] |
| lyst[a] | p[b] | T[c] | LHSV[d] | sion[e] | bitol | mannitol | fructose |
| A | 1500 | 120 | 0.25 | 97 | 95 | 3 | 0 |
| | | | 0.5 | 87 | 95 | 3 | 0 |
| | | | 1.0 | 73 | 96 | 2 | 0 |
| | 2000 | | 1.0 | 87 | 97 | 2 | 0 |
| | 2300 | 120 | 1.0 | 88 | 98 | 2 | 0 |
| | 700 | 130 | 1.0 | 81 | 93 | 4 | 1 |
| | 700 | 120 | 1.0 | 68 | 95 | 2 | 2 |
| | | | 0.5 | 92 | 95 | 4 | 1 |
| | | | 0.25 | 99 | 93 | 5 | 0 |
| | 1500 | 120 | 1.0 | 81 | 97 | 2 | 0 |
| | 2000 | 120 | 1.0 | 89 | 97 | 2 | 0 |
| | 700 | 120 | 1.0 | 64 | 96 | 2 | 2 |
| | 2000 | 110 | 2.5 | 49 | 98 | 1 | 1 |
| B | 700 | 120 | 0.5 | 98 | 92 | 6 | 0 |
| | 2000 | 120 | 2.5 | 77 | 97 | 2 | 0 |
| | | | 1.0 | 99 | 93 | 4 | 1 |
| | | | 0.5 | 99 | 91 | 5 | 0 |
| | 1500 | 120 | 1.0 | 99 | 93 | 3 | 0 |
| | 700 | 120 | 2.0 | 55 | 94 | 3 | 1 |
| | | | 1.0 | 84 | 93 | 4 | 1 |
| | 700 | 130 | 1.0 | 98 | 90 | 7 | 0 |
| | | 110 | 1.0 | 72 | 95 | 2 | 1 |
| | | 120 | | 86 | 92 | 4 | 1 |
| | 2300 | 120 | 0.5 | 99.9 | 92 | 4 | 0 |
| | | | 0.7 | 99.8 | 94 | 3 | 0 |

[a]Catalyst A or B of Example 2.
[b]Hydrogen pressure, psig.
[c]Temperature, °C.
[d]Liquid hourly space velocity.
[e]Percent glucose reacted.
[f]Selectivity is the percentage of any one product relative to total product formation.

The data show that sorbitol can be formed with a selectivity in excess of 95% at glucose conversions above 95%.

Samples of effluent were analyzed from time-to-time for alumium, titanium, and ruthenium. Analysis did not vary substantially over the course of the run, although they were somewhat dependent upon reaction conditions. 120° C., 2000 psig, and 1.0 LHSV effluent using Catalyst A showed 5.7 ppm Al, 4.0 ppm Ti, and less than 1 ppm Ru, whereas that using Catalyst B showed 3.6 ppm Al, and less than 1 ppm Ti and Ru.

EXAMPLE 4

Catalysts of nickel on titanated alumina were prepared in a fashion analogous to that described in Example 2, with reduction in hydrogen at 250 (Catalyst C) and 450° C. (Catalyst D), respectively. A mixture of 60 ml of a 45% aqueous solution of glucose containing 6 g of catalyst (10% Ni) was reacted with hydrogen at 700 psig and 120° C. for 5 hours. Product analysis is given in the following table.

| Catalyst | Conversion | sorbitol | Selectivity mannitol | fructose |
|---|---|---|---|---|
| C | 97 | 91 | 6 | — |
| D | 94 | 85 | 8 | 0.5 |

The data show unequivocally the effect of reducing the metal in hydrogen at different temperatures, with the lower temperature being advantageous.

EXAMPLE 5

Continuous reduction in a fixed bed reactor using a commercial nickel-on-kieselguhr catalyst was performed in a manner similar to that described in Example 3. Effluent was analyzed for nickel and silica at various periods with the results shown in the following table.

| | Dissolved Metal (ppm) | |
|---|---|---|
| Conditions | Ni | Si |
| 120° 1.0 LHSV 1500 psi $H_2$ | 355 | 165 |
| 130° | 397 | 162 |

-continued

| Conditions | Dissolved Metal (ppm) | |
| --- | --- | --- |
| | Ni | Si |
| 1.0 LHSV 1500 psi H$_2$ 130° | 420 | 152 |
| 0.5 LHSV 1500 psi H$_2$ 120° | 220 | 113 |
| 1.0 LHSV 1500 psi H$_2$ | | |

Thus, a commercial catalyst affords product with high levels of metal from the support (Si) and the catalytic component (Ni).

What is claimed is:

1. A method for the hydrogenation of a carbohydrate to its polyol(s) comprising at hydrogenation conditions an aqueous solution of the carbohydrate with hydrogen and a catalyst consisting essentially of a zerovalent Group VIII metal selected from the group consisting of osmium, rhodium, ruthenium, nickel, palladium and platinum dispersed on titanated alumina, and recovering the formed polyol(s).

2. The method of claim 1 where the carbohydrate is a monosaccharide.

3. The method of claim 2 where the monosaccharide is selected from the group consisting of hexoses, pentoses, and tetroses.

4. The method of claim 3 where the monosaccharide is a hexose and the polyol is a hexitol.

5. The method of claim 4 where the hexose is glucose or mannose and the hexitol is sorbitol or mannitol, respectively.

6. The method of claim 4 where the hexose is fructose and the polyol is a mixture of sorbitol and mannitol.

7. The method of claim 1 where the metal is ruthenium.

8. The method of claim 1 where the hydrogenation conditions include a hydrogen pressure from about 700 to about 5000 psig and a temperature from about 80° to about 160° C.

9. The method of claim 8 where the pressure is from about 1000 to about 3000 psig.

10. The method of claim 8 where the temperature is from about 100° to about 150° C.

11. The method of claim 10 where the temperature is from about 110° to about 130° C.

* * * * *